US008534839B2

(12) United States Patent
Meuse et al.

(10) Patent No.: US 8,534,839 B2
(45) Date of Patent: Sep. 17, 2013

(54) ADAPTIVE VISUAL PERFORMANCE TESTING SYSTEM

(75) Inventors: Patricia Ann Meuse, Mansfield, TX (US); Jenny Novotny Devenport, Belmont, CA (US); David Gary Kirschen, Brea, CA (US); Daniel Moses Laby, Canton, MA (US)

(73) Assignee: Alcon Research, Ltd., Fort Worth, TX (US)

( * ) Notice: Subject to any disclaimer, the term of this patent is extended or adjusted under 35 U.S.C. 154(b) by 148 days.

(21) Appl. No.: 13/033,930

(22) Filed: Feb. 24, 2011

(65) Prior Publication Data

US 2011/0211163 A1    Sep. 1, 2011

Related U.S. Application Data

(60) Provisional application No. 61/309,209, filed on Mar. 1, 2010.

(51) Int. Cl.
*A61B 3/00* (2006.01)
*A61B 3/032* (2006.01)

(52) U.S. Cl.
CPC ...................................... *A61B 3/032* (2013.01)
USPC .......................................... 351/246; 351/239

(58) Field of Classification Search
CPC ....................................................... A61B 3/032
USPC .......................... 351/222, 223, 246, 237–243
See application file for complete search history.

(56) References Cited

U.S. PATENT DOCUMENTS

| | | | |
|---|---|---|---|
| 5,059,127 A | 10/1991 | Lewis et al. | |
| 5,629,748 A | 5/1997 | Hayashi et al. | |
| 6,244,713 B1 | 6/2001 | Hayashi et al. | |
| 6,406,147 B1 | 6/2002 | Hayashi et al. | |
| 6,425,665 B2 | 7/2002 | Hayashi et al. | |
| 6,547,392 B2 | 4/2003 | Fujieda | |
| 7,537,343 B2 | 5/2009 | Kanazawa et al. | |
| 8,087,781 B2 | 1/2012 | Kanazawa et al. | |
| 2007/0218440 A1 | 9/2007 | Delahunt et al. | |
| 2008/0212032 A1* | 9/2008 | Seiller et al. | 351/246 |
| 2012/0092622 A1 | 4/2012 | Hirayama | |

FOREIGN PATENT DOCUMENTS

WO    WO 2011/109297 A1    9/2011

OTHER PUBLICATIONS

International Searching Authority, International Search Report, PCT/US2011/026484, Apr. 10, 2011, 2 pages.
International Searching Authority, International Preliminary Report on Patentability and Written Opinion of the International Searching Authority, PCT/US2011/026484, Apr. 19, 2011, 6 pages.

* cited by examiner

*Primary Examiner* — Huy K Mai
(74) *Attorney, Agent, or Firm* — Jonathan E. Prejean

(57) ABSTRACT

A method of testing visual performance includes determining a difficulty rating for each of a plurality of visual recognition tests. The method further includes displaying one of the visual recognition tests to a subject and receiving from the subject a response to the visual recognition test. After receiving the response to the visual recognition test, a subsequent visual recognition test is selected to have a difficulty rating determined based on the response received from the subject, the subsequent visual recognition test is displayed, and a response is received from the subject. The subsequent visual recognition tests are repeated until a predetermined number of responses is reached. A visual performance score is determined based on the set of responses received from the subject and the difficulty ratings for the visual recognition tests displayed to the subject is then output.

16 Claims, 2 Drawing Sheets

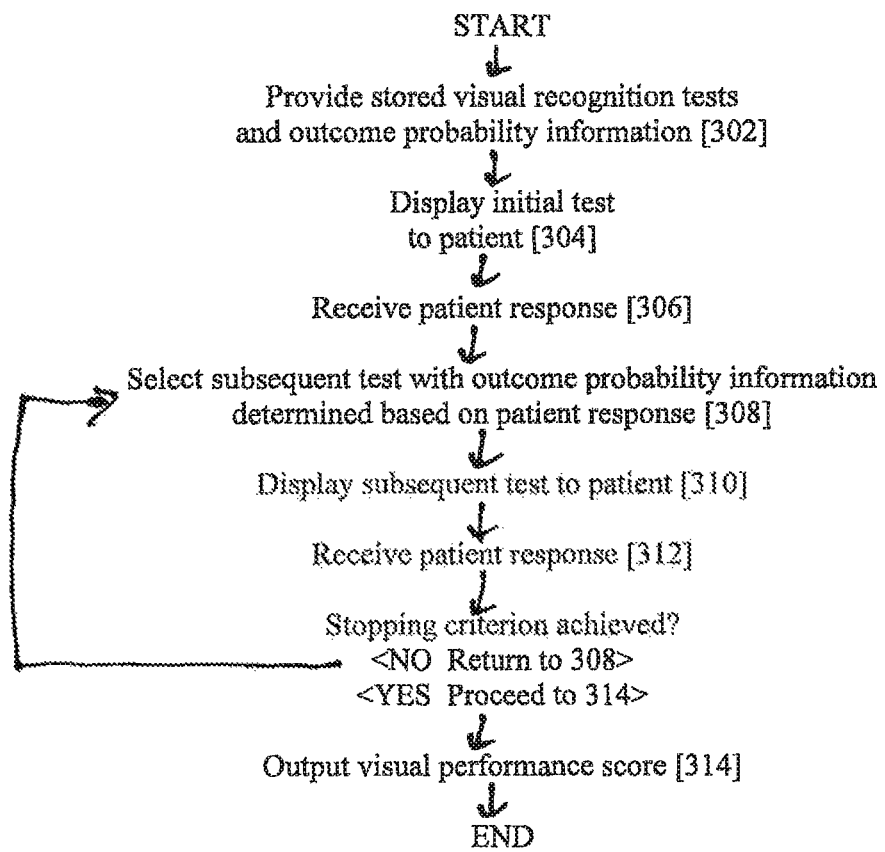

ADAPTIVE VISUAL PERFORMANCE TESTING SYSTEM

RELATED APPLICATIONS

This application claims priority to U.S. provisional application Ser. No. 61/309,209, filed on Mar. 1, 2010, the contents which are incorporated herein by reference.

TECHNICAL FIELD OF THE INVENTION

The present invention relates to methods of testing vision and more particularly to an adaptive visual performance testing system.

BACKGROUND OF THE INVENTION

Visual performance testing presents a number of challenges. While visual function is currently assessed in clinical and research settings by objective measurements (e.g., visual acuity testing, contrast sensitivity testing), these measurements do not always provide an accurate indication of subjects' visual function in a practical sense. One drawback of these methods is that they typically test only one or two aspects of vision at a time (target size, percent contrast). Real world visual function consists of responding based on multiple characteristics of a visual target (e.g., size, percent contrast, motion or speed, color, etc.). Even if multiple visual tests are performed, each test is tailored to the specific aspect that it measures, so that a holistic sense of visual performance is not obtained.

Even existing tests that attempt to evaluate visual function using representative activities of daily life have shortcomings. An example is testing visual performance using a driving simulator. The complexity of the apparatus often makes testing expensive, requiring subjects to travel to a particular location which can be remote from their physician's office. Additionally, the testing experience often includes tasks requiring more complex cognitive and physical function than simply vision. For example, in some driving simulators subjects must literally sit behind the wheel/windshield and operate controls in response to stimuli—this requires the coordination of visual processing and physical responses. Thus this testing scenario does not achieve a pure assessment of visual function.

Based on the available tests, there remains a need for visual performance measurement that is more consistent with real world function.

SUMMARY OF THE INVENTION

Various embodiments of the present invention provide an adaptive visual performance testing system that translates subject responses to visual targets having varying outcome probability information (e.g., difficulty, discrimination) into measures of visual performance (ability). In certain embodiments of the present invention, a method of testing visual performance includes:

(a) providing a memory storing a plurality of visual recognition tests and outcome probability information associated with the visual recognition test;

(b) displaying one of the visual recognition tests to a subject;

(c) receiving from the subject a response to the visual recognition test;

(d) after receiving the response to the visual recognition test, selecting a subsequent visual recognition test having selected outcome probability information determined based on the response from the subject;

(e) displaying the subsequent visual recognition test;

(f) receiving from the subject a response to the subsequent visual recognition test;

(g) repeating steps (d)-(f) until a stopping criterion is achieved; and (h) outputting a visual performance score determined based on the set of responses received from the subject and the outcome probability information for the visual recognition tests displayed to the subject.

In particular embodiments of the present invention, software embodied in a computer-readable medium may be executable by a processor to cause the steps of such a method to be performed. In other embodiments, an adaptive visual performance testing system includes a memory storing a plurality of visual recognition tests and outcome probability information associated with each visual recognition test, a display operable to display an image for each of the visual recognition tests to a subject, an input device operable to receive a response to each of the visual recognition tests from the subject, and a processor operable to execute instructions stored in the memory to perform the steps of such a method.

BRIEF DESCRIPTION OF THE FIGURES

A more complete understanding of the present invention and the advantages thereof may be acquired by referring to the following description, taken in conjunction with the accompanying drawings in which like reference numbers indicate like features.

FIG. 2 is a flow chart illustrating an example method of testing visual performance according to a particular embodiment of the present invention.

DETAILED DESCRIPTION OF PREFERRED EXEMPLARY EMBODIMENTS

Figure 1:
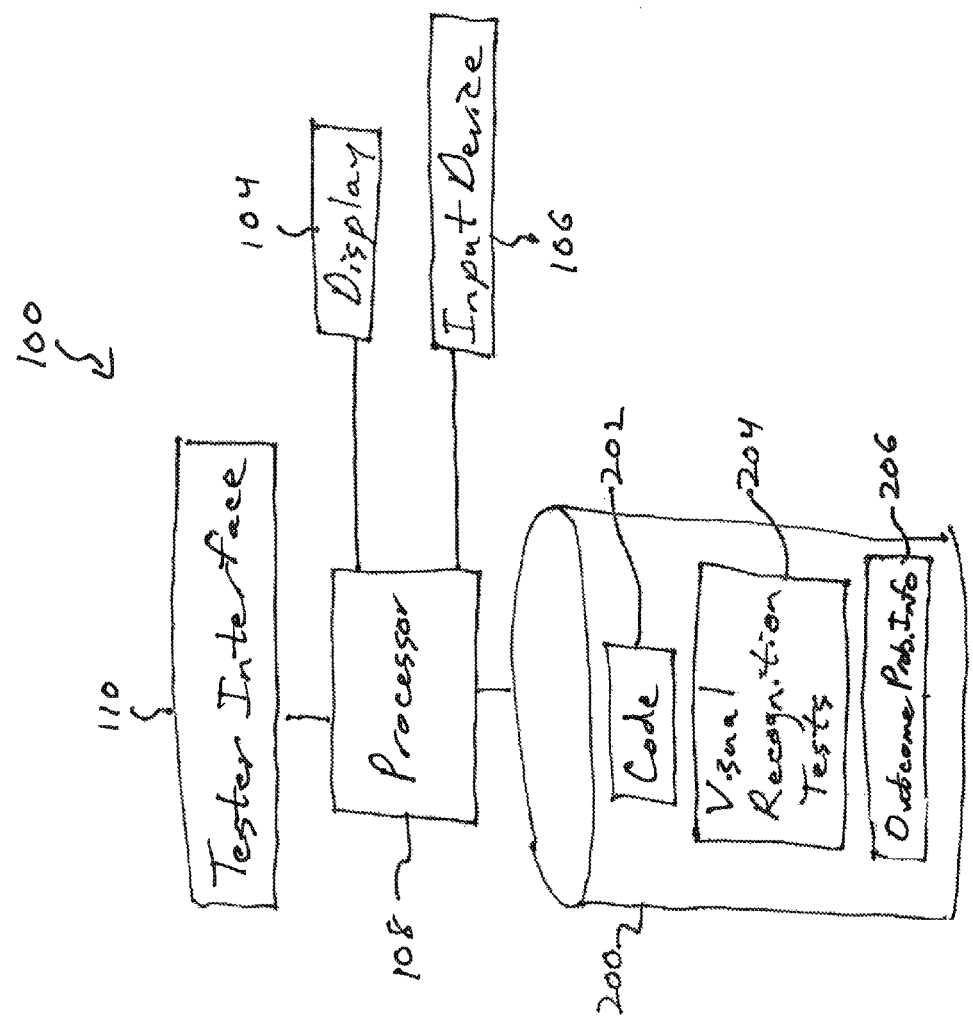
FIG. 1 is block diagram of an adaptive visual performance testing system according to a particular embodiment of the present invention.

Various embodiments of the disclosure are illustrated in the FIGURES, like numerals being generally used to refer to like and corresponding parts of the various drawings. As used herein, the terms "comprises," "comprising," "includes," "including," "has," "having" or any other variation thereof, are intended to cover a non-exclusive inclusion. For example, a process, article, or apparatus that comprises a list of elements is not necessarily limited to only those elements but may include other elements not expressly listed or inherent to such process; article, or apparatus. Further, unless expressly stated to the contrary, "or" refers to an inclusive or and not to an exclusive or.

Additionally, any examples or illustrations given herein are not to be regarded in any way as restrictions on, limits to, or express definitions of, any term or terms with which they are utilized. Instead, these examples or illustrations are to be regarded as being described with respect to one particular embodiment and as illustrative only. Those of ordinary skill in the art will appreciate that any term or terms with which these examples or illustrations are utilized will encompass other embodiments which may or may not be given therewith or elsewhere in the specification and all such embodiments are intended to be included within the scope of that term or terms. Language designating such nonlimiting examples and illustrations includes, but is not limited to: "for example", "for instance", "e.g.", "in one embodiment".

FIG. 1 is a block diagram of a visual performance testing system 100 according to a particular embodiment of the present invention. The system 100 includes a subject interface comprising a display 104 and an input device 106. The display 104 may be any suitable means for producing a visually perceptible image for a subject, such as a monitor. The input device 106 includes one or more components suitable for receiving responses from a subject, such as a push button, a keyboard, a mouse, or any other suitable input device. A timer may also be associated with the input device 106 so that the time interval required for the subject to provide a response can be measured. In various embodiments, the system 100 may include multiple input devices for receiving different forms of response from the subject.

The system 100 also includes a processor 108 and a memory 200 that stores instructions executable by the processor, hereinafter referred to as "code" 202. The memory 200 may include any suitable form of information storage, whether volatile or non-volatile, including but not limited to electronic, magnetic, or optical memory. The processor 108 may include one or more microprocessors, microcontrollers, programmable devices, or other suitable components for processing information and executing instructions to cause various functions of the system 100, including any of those functions described herein, to be performed. In particular, the processor 108 can generate an output at a tester interface 110 of a visual performance score for the subject. The output can be produced in any suitable format for the tester interface 110, including a visual display on a monitor, a paper printout, colored lights, audible reports generated by a speech synthesizer, or other output methods known to those skilled in the art. The processor 108 may also receive selections of output format through the tester interface 110, as well as other information allowing the user to control the operation of the system 100.

The memory 200 also stores information pertaining to a set of visual recognition tests 204 and associated outcome probability information 206 for each of the visual recognition tests 204. The outcome probability information 206 can be collected using statistically controlled analysis of subject responses, for example. In various embodiments of the present invention, the visual recognition tests 204 provide a visually perceptible image to a subject using the display 104, and the subject provides a suitable response using the input device 106. In this context, "recognition" can refer to any suitable subject response to the display of the image. For example, the subject can be tested to determine whether he can distinguish the image at all. In another example, the subject can be asked to distinguish between a number of alternatives, such as identifying the color, shape, or orientation of the object. Commonly used images known in the art of visual testing include the orientation of a letter "E" or a Landoldt C, wherein the subject indicates the orientation of the image (up, down, left, right) using a four-key pad as the input device 106.

In particular, the visual recognition tests 204 may advantageously be designed to vary an image parameter affecting the probability of visual recognition, which is in turn used to assign outcome probability information 206 to the test 204. Using responses from a wide range of visual abilities of subjects, the outcome probability information 206 of each test may be estimated. For example, smaller objects are ordinarily more difficult to distinguish than larger objects, so a test 204 that requires the subject to recognize an object when it is seen and to respond within a certain time period will be made more difficult by using smaller images. Alternatively, the time period for presentation of the image may be varied to alter the difficulty of the task. Image parameters can be varied within the test 204 or between tests 204. In one example of the former type of test 204, an image can begin at a small size and can be enlarged over time, and the subject's success at recognition is assessed based on the time at which the subject recognizes the image. In an example of the latter, different visual tests 204 can display the same image at different sizes, and the subject's success at recognition can be assessed based on whether the image of a particular size is recognized by the subject.

The visual recognition tests 204 can also advantageously vary a number of different image parameters that affect the difficulty of image recognition and, therefore, may optimally distinguish levels of visual ability. For example, image parameters such as image contrast, color, and apparent rate of motion can be varied along with image size. Advantageously, the algorithm used for the display 104 can allow image parameters to be systematically varied to modify these image parameters, and a high-resolution display 104 can be used to enable finer measurements of contrast variation and the like. Additional visual effects, such as the presence of distractors or glare in the image, can also be evaluated for their effects on visual performance. Particular embodiments of the present invention can advantageously use the outcome probability information 206 across tests 204 varying a number of different image parameters and the response vectors to determine an overall visual performance score that provides a more holistic indication of visual performance for a variety of different visual recognition tasks that are performed in daily life. As noted previously, the user may also be allowed to customize the testing process, including the selection of particular visual recognition tests 204, using the tester interface 110.

Various embodiments of the present invention employ an adaptive testing procedure, which is to say that subsequent visual recognition tests 204 given to the subject are determined based on the subject's performance on a previous visual recognition tests 204. In particular, subsequent tests 204 can be chosen at an appropriate level of outcome probability information 106 based on the subject's current estimated ability. Thus, for example, a test 204 with comparable outcome probability information 206 but using a different visual recognition task could be selected. In another example, a visual recognition test 204 could be selected with outcome probability information 206 to better match a subject's current estimated ability if the subject did not successfully respond to the previous visual recognition test 204. This adaptive gradation of outcome probability information 206 allows testing to include tests that are appropriate to each subject's level of ability, so that the subject is not given a large number of tasks that are too difficult or too easy given the current estimate of ability level. Therefore, the adaptive testing process allows the subject's visual performance to be tested efficiently and in a way that may provide a better overall indication of the subject's visual function in daily activities.

The visual performance score can be determined based on the responses to the tests 204 and the outcome probability information 206 of the tests 204 when a predetermined number of responses has been received. In particular examples, the score can be determined for multiple tasks having different difficulty levels using an item response theory (IRT) scoring algorithm. In its simplest form, the Rasch equation gives a probability of success (also called item response function) for a person having a certain level of ability as follows:

$$p_{ij}(\theta_j) = \frac{1}{1 + e^{(\theta_j - b_i)}}$$

wherein $p_{ij}(\theta^j)$ is a probability of success for a person of ability $\theta_j$ to correctly respond to an item of difficulty $b_i$.

The equation can be further modified for tasks that may not be equally discriminatory among abilities, where a is the degree to which a task discriminates between people with different ability levels, as follows:

$$p_{ij}(\theta_j) = \frac{1}{1 + e^{ai(\theta_j - b_i)}}$$

The probability of correctly guessing an answer can further be incorporated into the equation as a guessing parameter c:

$$p_{ij}(\theta_j) = c + \frac{(1-c)e^{ai(\theta_j - b_i)}}{1 + e^{ai(\theta_j - b_i)}}$$

Ability can be estimated using item response functions that consider both the item parameters and the subject's set of correct and incorrect responses. This information can also be used in the adaptive test selection process to estimate visual performance more efficiently and to further improve reliability of the performance score. Such techniques are known in cognitive testing, such as the adaptive testing used in standardized college admission tests, but the application to visual performance testing and the evaluation of characteristics (e.g., difficulty, discrimination) for visual recognition tasks is not found in conventional testing. On the contrary, considerable effort is devoted in cognitive testing to overcoming difficulties in visual performance so that even people with visual impairments can be adequately tested for cognitive ability.

FIG. 2 is a flow chart 300 showing an example method for testing visual performance according to a particular embodiment of the present invention. At step 302, a memory is provided with a plurality of visual recognition tests and associated outcome probability information for each test. At step 304, one of the visual recognition tests is displayed to a subject. At step 306, a response is received from the subject.

After the response is received, the method proceeds to step 308, wherein a subsequent visual recognition test is selected to have outcome probability information determined based on the subject's response. The selected visual recognition test is then displayed to the subject at step 310, and a response is received from the subject at step 312. In decision step 314, a determination is made of whether a stopping criterion has been achieved. For example, stopping criteria could include reaching a predetermined number of responses, achieving a predetermined level of statistical significance in the responses, or other similar standards for determining when the information collected adequately indicates the subject's visual performance. The stopping criterion may also be a combination of such standards, so that the stopping criterion is considered to be achieved when each of the standards is achieved, when a total score based on all of the standards is reached, etc. If the stopping criterion is achieved, then steps 308, 310, and 312 can be repeated until enough responses are received.

Once the predetermined number of responses is received, an output including a visual performance score determined from the responses and the outcome probability information of the visual recognition tests is generated at step 314. In particular embodiments, the visual performance score can be a single numerical rating or "pass/fail" output. In alternative embodiments, the visual performance score can include separate scores for different visual tasks as well. In general, any suitable form of scoring output that takes into account responses collected during adaptive testing with varying outcome probability information would be consistent with the present invention.

Although embodiments have been described in detail herein, it should be understood that the description is by way of example only and is not to be construed in a limiting sense. For example, while a particular example of a testing method has been presented, it should be understood that the testing method could also be modified in a manner consistent with any of the various test selection methods and image parameter variations described herein. It is to be further understood, therefore, that numerous changes in the details of the embodiments and additional embodiments will be apparent to, and may be made by, persons of ordinary skill in the art having reference to this description. It is contemplated that all such changes and additional embodiments are within scope of the claims below and their legal equivalents.

What is claimed is:

1. A method of testing visual performance, comprising:
    (a) providing a memory storing a plurality of visual recognition tests and outcome probability information associated with the visual recognition test;
    (b) displaying one of the visual recognition tests to a subject;
    (c) receiving from the subject a response to the visual recognition test;
    (d) after receiving the response to the visual recognition test, selecting a subsequent visual recognition test having selected outcome probability information determined based on the response from the subject;
    (e) displaying the subsequent visual recognition test;
    (f) receiving from the subject a response to the subsequent visual recognition test;
    (g) repeating steps (d)-(f) until a stopping criterion is achieved; and
    (h) outputting a visual performance score determined based on the set of responses received from the subject and the outcome probability information for the visual recognition tests displayed to the subject.

2. The method of claim 1, wherein the visual performance score is determined using an item response theory (IRT) model.

3. The method of claim 1, wherein the visual recognition tests are selected to vary at least one image parameter selected from a group consisting of the following image parameters: size, contrast, color, orientation, presentation time, and apparent rate of motion.

4. The method of claim 3, where the outcome probability information for each test is based on the variation in the selected image parameter.

5. The method of claim 3, wherein the visual recognition tests are selected to vary at least two different image parameters.

6. The method of claim 1, wherein the visual recognition tests comprise presenting images with distractors or glare.

7. The method of claim 1, wherein the outcome probability information for the subsequent visual recognition tests is determined based on a current estimate of subject ability.

8. The method of claim 1, wherein the visual performance score is further determined based on a probability of guessing correctly.

9. Software embodied in a computer-readable medium operable, when executed by a processor, to cause the following steps to be performed:
 (a) providing a memory storing a plurality of visual recognition tests and outcome probability information associated with the visual recognition test;
 (b) displaying one of the visual recognition tests to a subject;
 (c) receiving from the subject a response to the visual recognition test;
 (d) after receiving the response to the visual recognition test, selecting a subsequent visual recognition test having selected outcome probability information determined based on the response from the subject;
 (e) displaying the subsequent visual recognition test;
 (f) receiving from the subject a response to the subsequent visual recognition test;
 (g) repeating steps (d)-(f) until a stopping criterion is achieved; and
 (h) outputting a visual performance score determined based on the set of responses received from the subject and the outcome probability information for the visual recognition tests displayed to the subject.

10. The software of claim 9, wherein the visual performance score is determined using an item response theory (IRT) model.

11. The software of claim 9, wherein the visual recognition tests are selected to vary at least one image parameter selected from a group consisting of the following image parameters: size, contrast, color, orientation, presentation time, and apparent rate of motion.

12. The software of claim 11, where the outcome probability information for each test is based on the variation in the selected image parameter.

13. The software of claim 11, wherein the visual recognition tests are selected to vary at least two different image parameters.

14. The software of claim 9, wherein the visual recognition tests comprise presenting images with distractors or glare.

15. The software of claim 9, wherein the outcome probability information for the subsequent visual recognition tests is determined based on a current estimate of subject ability.

16. The software of claim 9, wherein the visual performance score is further determined based on a probability of guessing correctly.

* * * * *